United States Patent [19]

Edwards et al.

[11] Patent Number: 5,558,673

[45] Date of Patent: Sep. 24, 1996

[54] MEDICAL PROBE DEVICE AND METHOD HAVING A FLEXIBLE RESILIENT TAPE STYLET

[75] Inventors: Stuart D. Edwards, Los Altos; Ronald G. Lax, Grass Valley, both of Calif.

[73] Assignee: Vidamed, Inc., Menlo Park, Calif.

[21] Appl. No.: 316,318

[22] Filed: Sep. 30, 1994

[51] Int. Cl.$^6$ .................................................. A61B 17/39
[52] U.S. Cl. .............................. 606/41; 606/45; 606/48; 604/22; 607/101
[58] Field of Search ........................... 606/29–31, 37–42, 606/45–50; 128/642; 604/21, 22; 607/100–102, 115, 116

[56] References Cited

U.S. PATENT DOCUMENTS

| | | | |
|---|---|---|---|
| 4,522,212 | 6/1985 | Gelinas et al. | 128/642 |
| 4,565,200 | 1/1986 | Cosman | 606/50 |
| 5,007,908 | 4/1991 | Rydell | 606/50 |
| 5,336,222 | 8/1994 | Durgin, Jr. et al. | 606/50 |
| 5,385,544 | 1/1995 | Edwards et al. | 606/47 |
| 5,403,311 | 4/1995 | Abele et al. | 606/50 |

*Primary Examiner*—Angela D. Sykes
*Assistant Examiner*—Michael Peffley
*Attorney, Agent, or Firm*—Flehr, Hohbach, Test, Albritton & Herbert

[57] ABSTRACT

The device and method of the present invention is a medical probe device which has an elongated guide having a longitudinal axis, and a handle and probe end, the guide defining a port at its probe end. The device also has a flexible, resilient tape stylet, movably mounted relative to said longitudinal guide for movement along the longitudinal axis, having two opposed side portions, a proximal end, a piercing end and a sharpened tip on said piercing end, and a deflector, housed within said longitudinal guide, which deflects said flexible resilient tape stylet through said port. A method of moving a stylet through an elongated guide to an outlet port is also disclosed. A method of manufacturing a flexible resilient tape stylet of the present invention is also disclosed.

25 Claims, 6 Drawing Sheets

FIG_1

FIG_2

FIG_3

FIG_4

FIG_5

FIG_6

FIG_7

FIG_8

FIG_9

FIG_10

FIG_11

FIG_12

FIG_13

FIG_14

FIG_15

FIG_16

*FIG_17*

*FIG_18*

*FIG_19*

5,558,673

MEDICAL PROBE DEVICE AND METHOD HAVING A FLEXIBLE RESILIENT TAPE STYLET

FIELD OF THE INVENTION

The invention relates generally to a device and method for the ablative treatment of tissues. In particular, the invention relates to a device and method for ablative treatment of tissues wherein a flexible resilient tape stylet is used to ablate diseased tissues.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above 300 kHz in order to avoid any adverse effects such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radio frequency, acoustical (ultrasound) and light energy (laser) devices have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions. These devices also have a sleeve which covers the electrode or antenna and is used to control the amount of ablation which occurs by exposing only a selected portion of the electrode or antenna. This sleeve is often hard to manufacture and often causes friction when it contact the electrode or antenna. The sleeve can also cause tissue damage as it is slid forward. Finally, the sleeve can be easily damaged during tissue penetration since the sleeve is very thin. In addition, these prior art devices have a single continuous electrode or antenna so that smaller discrete segments of the electrode can not be selectively energized. In addition, these single electrodes can not penetrate tissue and require a needle to do so.

OBJECTS AND SUMMARY OF THE INVENTION

It is therefore an object of the present invention to provide a sleeveless medical probe device.

It is another object of the present invention to provide a medical device which can have multiple electrodes which can be energized independently.

It is another object of the present invention to provide a medical probe device which has multiple electrodes and multiple thermocouples, the multiple thermocouples being located in close proximity to the electrodes.

It is another object of the present invention to provide a medical probe device which has a flexible resilient tape stylet which is initially rigid to bending, but can be temporarily deformed to allow the tape spear to be bent, and then returned to its rigid nature.

It is another object of the present invention to provide a medical probe device and method wherein the medical probe enters the body through a natural orifice such as the urethra. Once inside the body, the flexible resilient tape stylet pierces the urethra and enters the tissue to be treated, such as the prostate. Since the electrodes are independently energizable and do not extend the entire length of the tape stylet, only the prostate tissue is ablated and the urethra wall does not suffer any further damage.

In summary, the device and method of the present invention is a medical probe device which has an elongated guide having a longitudinal axis, and a proximal and distal end, the guide defining a port at its distal end. The device also has a flexible, resilient tape stylet, movably mounted relative to said longitudinal guide for movement along the longitudinal axis, the tape stylet having two opposed side portions, a proximal end, a distal end and a sharpened tip on said distal end, and a deflector, housed within said longitudinal guide, which deflects said flexible resilient tape stylet through said port.

The device may also have a handle which houses various control mechanism which control the amount and angle of the flexible resilient tape stylet exposed to the target tissue.

A method of moving a stylet through an elongated guide to an outlet port is also disclosed.

DETAILED DESCRIPTION OF THE INVENTION

The device of this invention provides a precise controlled positioning of a treatment tape stylet in a tissue targeted for treatment or destruction from a catheter positioned in the vicinity of the target tissue.

The term "stylet" as used hereinafter is defined to include both solid and hollow probes which are adapted to be passed from a catheter port through normal tissue to a target tissue. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiberoptic cable. The stylet preferably has a sharpened end to reduce resistance and trauma when it is pushed through tissue to a target site.

The stylet can be designed to provide a variety of medically desired treatments of a selected tissue. As a radio frequency electrode or microwave antenna, it can be used to ablate or destroy the target tissue. As a hollow tube, it can be used to deliver a treatment fluid such as a liquid to a target tissue. The liquid can be a simple solution or a suspension of solids, for example, colloidal particles, in a liquid. Since the stylet is very thin, it can be directed from the catheter through intervening normal tissue with a minimum of trauma to the normal tissue.

In the preferred embodiments of the present invention, the stylet is a flexible resilient tape stylet which is capable of puncturing tissues. The flexible resilient tape stylet is made of a flexible resilient material which has a high elastic limit so that the flexible resilient tape stylet can be deformed and then return to its original configuration without any permanent damage. The flexible resilient tape stylet of the present invention is not limited to the shapes disclosed in the preferred embodiments and may be any shape which has the required characteristics of being strong enough in a non-deformed configuration to puncture tissue yet temporarily deformable such that it is able to bend around a 90 degree turn without exceeding the elastic limit of the flexible resilient tape stylet.

Figure 1:
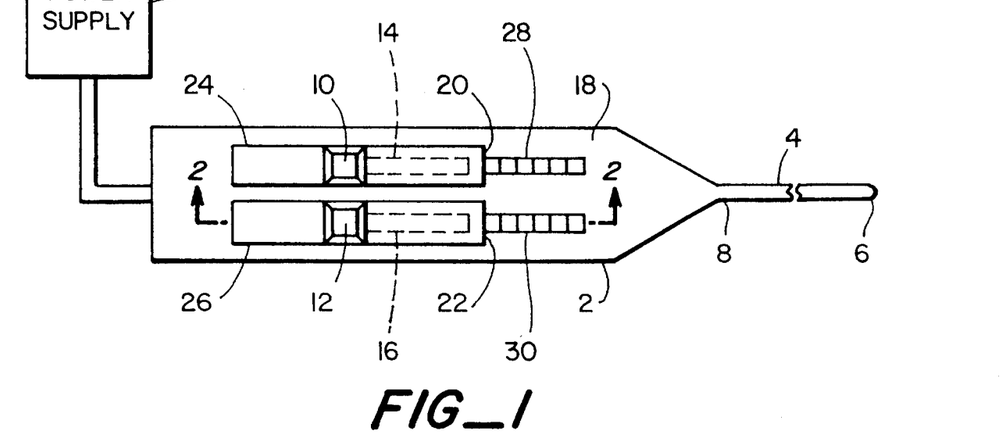
FIG. 1 is a top view of a radio frequency (RF) ablative device of the present invention having a handle portion and an elongated guide.

Referring to the drawings, FIG. 1 is a planar view of a medical probe device having a flexible resilient tape stylet of this invention. The device has a handle 2 and an elongated guide 4. The elongated guide may be a catheter. The elongated guide 4 has a probe end 6 and a handle end 8. The probe end 6 corresponds to a catheter tip. A tape stylet manual control tab 10 and a roller manual control tab 12 are mounted for sliding engagement in slots 14 and 16 in the handle top plate 18. The tape stylet manual control tab 10 and the roller manual control tab 12 can be any digit applicator which permits a human digit to manipulate a controller, such as a tab, or a projection, or a depression. The position of the distal edges 20 and 22 of the tab slides 24 and 26 with their respective index strips 28 and 30 independently indicate the advancement and retraction of the flexible resilient tape stylet and roller.

The handle 2 is also electrically connected to a power supply 31. The power supply 31 provides energy to the medical probe. The operation of the power supply 31 will be described in more detail below.

Figure 2:
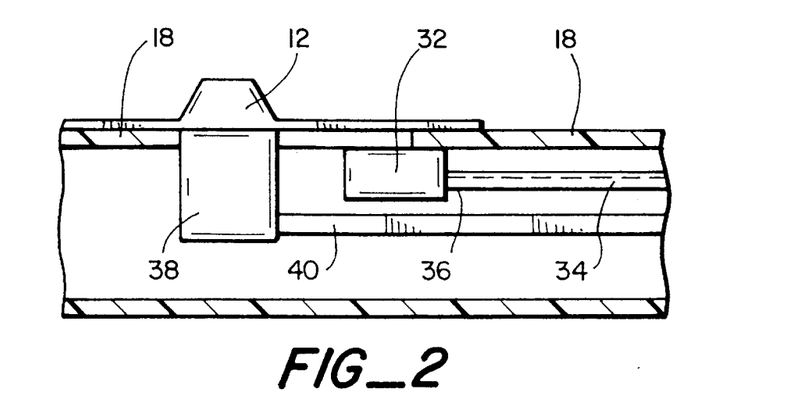
FIG. 2 is a fragmentary cross section taken along line 2—2 in FIG. 1 of the handle portion showing a control mechanism.

FIG. 2 is a fragmentary cross-sectional view of the manual control portion of the handle of the medical probe device shown in FIG. 1, taken along the line 2—2. The tape stylet manual control tab 10 (not shown since it is obscured by the roller manual control tab) is connected to a tape stylet connector 32 which is connected to a proximal end 36 of a flexible resilient tape stylet 34. Thus, linear motion of the tape stylet manual control tab 10 causes linear motion of the flexible resilient tape stylet 34. The roller manual control tab 12 is connected to a roller connector 38 which is connected to the proximal end of a roller yoke 40. The roller yoke 40 is rotatably connected to a roller 42 (shown in FIG. 5). Thus, similarly, linear motion of the roller manual control tab 12 causes linear motion of the roller 42.

Individual movement of the manual control tabs 10 and 12 provide individual advancing and retracting movement of the respective flexible resilient tape stylet 34 and of the roller 42. Indexing strips 28 and 30 provide reference points for controlled positioning of the control tabs 10 and 12, permitting precise, independent positioning of the flexible resilient tape stylet and the roller for controlled ablation of remote body portions as is explained in greater detail hereinafter.

The linear movement of the roller 42 operates to change the angle of the flexible resilient tape stylet 34 with respect to the elongated guide 4. The operation of the roller will be described in more detail below with reference to FIGS. 17–19.

Figure 3:
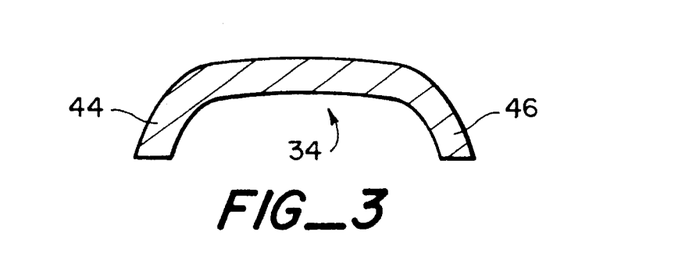
FIG. 3 is a cross sectional view of a flexible resilient tape stylet of the present invention which has a curved cross section.

The flexible resilient tape stylet 34 is preferably made of a flexible resilient material such as nickel-titanium alloy, tempered steel or reinforced plastic. The flexible resilient tape stylet 34 can be manufactured out of any material which has a high elastic limit so that the tape stylet can be temporarily deformed without any permanent damage yet have sufficient rigidity to puncture tissue. For the present invention, a flexible resilient tape stylet 34 which has two opposed side portions 44 and 46 will be used. The flexible resilient tape stylet 34 can be formed into the desired shape by any conventional means. FIG. 3 shows an embodiment of a flexible resilient tape stylet. This embodiment of the flexible resilient tape stylets has a pair of opposed side portions 44 and 46. In fact, any other shaped flexible resilient tape stylet which has a pair of opposed side portions can also be used since it is the opposed side portions which provide columnar lateral stiffness. This columnar lateral stiffness provides stiffness and rigidity to the flexible resilient tape stylet. However, when any section of the flexible resilient tape stylet is flattened out so that no opposed side portions exist, the flattened out section becomes flexible and can be bent without exceeding the elastic limit of the materials.

FIG. 3 shows the preferred embodiment of a flexible resilient tape stylet which has a curved cross section. As shown, the opposed side portions 44 and 46 are rounded. The amount of curvature of the opposed side portions 44 and 46 can vary greatly. The opposed side portions 44 and 46 in this embodiment both are actually part of one continuous arc. The curved cross section flexible resilient tape stylet will be used for all descriptions, but the invention is not limited to curved cross section flexible resilient tape stylets.

The characteristics of the flexible resilient tape stylet of the present invention will now be described in more detail. In its non-deformed shape, i.e., having two opposed side portions as defined above, the flexible resilient tape stylet 34 has longitudinal rigidity and can puncture tissue. If, however, the two opposed side portions are spread apart, such that the distance between the terminal edges of the opposed side portions is increased, the flexible resilient tape stylet is flattened out. When the flexible resilient tape stylet is flattened out, the two opposed side portions lie in the same plane as the rest of the flexible resilient tape stylet and the flexible resilient tape stylet becomes temporarily deformed and can bend easily. After the flexible resilient tape stylet has been bent and resumes a straight path, it will return to its non-deformed longitudinally rigid configuration having opposed side portions. The flexible resilient tape stylet 34 of the present invention remains in its rigid configuration having two opposed side portions unless it is deformed. It should be noted that the elastic limit of the material used to manufacture the flexible resilient tape stylet is not exceeded such that the flexible resilient tape stylet will return to its original shape after every deformation.

Figure 4:
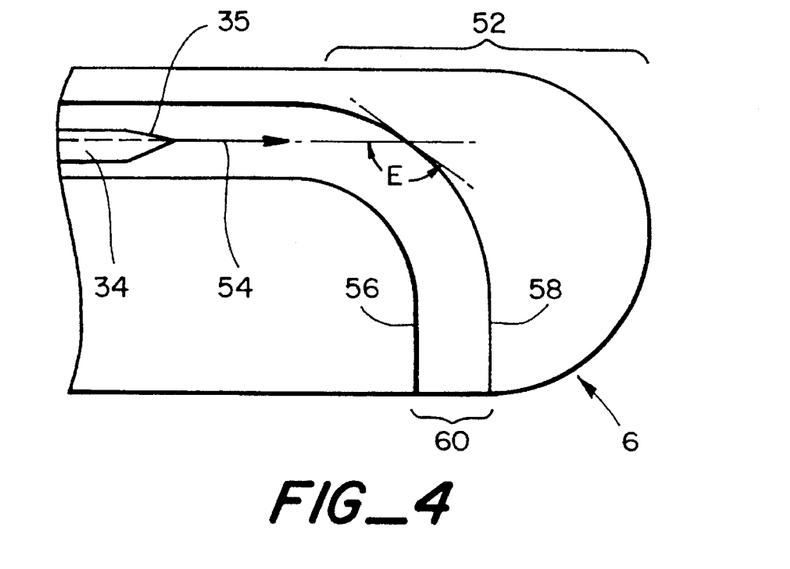
FIG. 4 is a fragmentary side view of another embodiment of the probe end of the elongated guide showing the angle between the direction of motion of the flexible resilient tape stylet and a deflector.

FIG. 4 is a fragmentary side view of the probe end of the elongated guide which shows how a deflector 52 is mounted with respect to the motion of the flexible resilient tape stylet and how the flexible resilient tape stylet is bent by the deflector 52. The flexible resilient tape stylet 34 moves longitudinally along the elongated guide 4 in a path as shown by arrow 54 until it runs into a deflector 52. The flexible resilient tape stylet 34 may have a sharpened, beveled tip 35. The sharpened, beveled tip 35 is beveled back away from the sharpened tip so that it can puncture tissue, but will not be damaged when it encounters the deflector 52. In this embodiment, the deflector 52 is a pair of curved side walls 56 and 58 which deform the flexible resilient tape stylet by deflecting the flexible resilient tape stylet 34 from a longitudinal direction to a lateral direction and through a port 60. The angle, E, is formed between the direction of initial motion of the flexible resilient tape stylet and the angle of the deflector 52. For this example where curved side walls 56 and 58 are used to deflect the flexible resilient tape stylet 34, the angle of the side wall 58 is measured by the tangent to the curve as shown. For the present invention, the angle, E, must be greater than or equal to 90° and less than 180°. Preferably, the angle E is greater than 90°, but less than 150°. Thus, the deflector 52 may be a vertical end wall (E=90°), a single curved wall, a pair of curved walls (shown in FIG. 4) or the combination of a roller and a curved wall (shown in FIG. 5). All of these different deflectors perform the required deformation and deflection of the flexible resilient tape stylet. In the preferred embodiment of the present invention, as shown in FIG. 5, the deflector 52 is a roller 42 in combination with a pair of spreader blocks 66 and 68.

Figure 5:
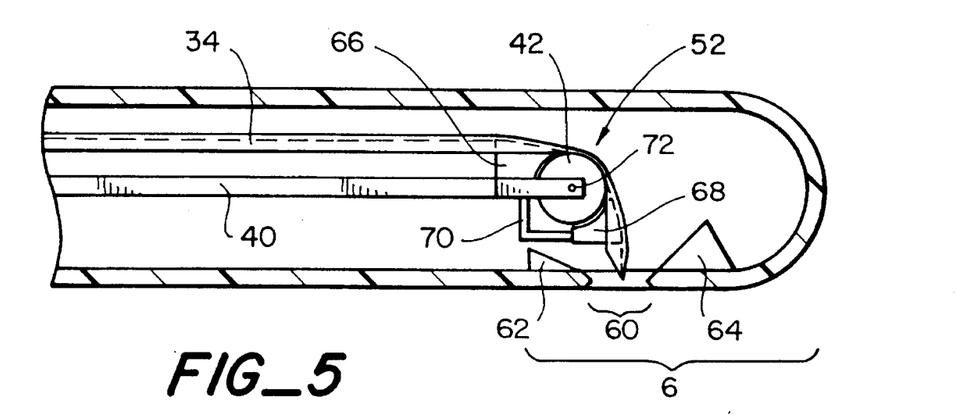
FIG. 5 is a fragmentary close-up cross section of the probe end of the elongated guide shown in FIG. 1 showing the internal structure which is housed within the elongated guide.

FIG. 5 is a side view of the preferred embodiment of the probe end of the medical probe device with a flexible resilient tape stylet. The probe end 6 houses guiding blocks 62 and 64 which guide the flexible resilient tape stylet 34 out of a port 60 which is located near the probe end 6. It should be understood that the elongated guide 4 can also be any guide which can support the flexible resilient tape stylet 34 and house a deflector 52. For example, the elongated guide in the preferred embodiment of the present invention is a catheter. The flexible resilient tape stylet 34 travels longitudinally along a guide (not shown). At the probe end 6, the flexible resilient tape stylet impinges upon a deflector 52. The deflector 52 has a first spreader block 66, a roller 42 and a second spreader block 68. The roller 42 is rotatably connected to a roller yoke 40 by an axle 72. The spreader blocks 66 and 68 are also supported and connected to the roller yoke 40 either directly or by a connector 70.

Figure 6:
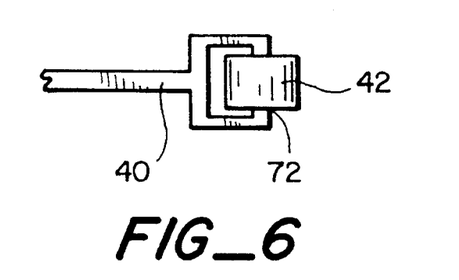
FIG. 6 is a fragmentary top view of the roller and yoke as shown in FIG. 5.

FIG. 6 shows a top view of the roller and its yoke. As described above, the roller 42 is rotatably connected to the yoke 40 by an axle 72. In this drawing, the spreader blocks 66 and 68 are not shown. The yoke 40 is in turn rigidly connected to the roller connector 38 and the roller manual control tab 12 which are located in the handle 2 (shown in FIG. 2). Thus, linear movement of the roller manual control tab 12 causes linear movement of the roller 42 which will be described below in more detail.

Figure 7:
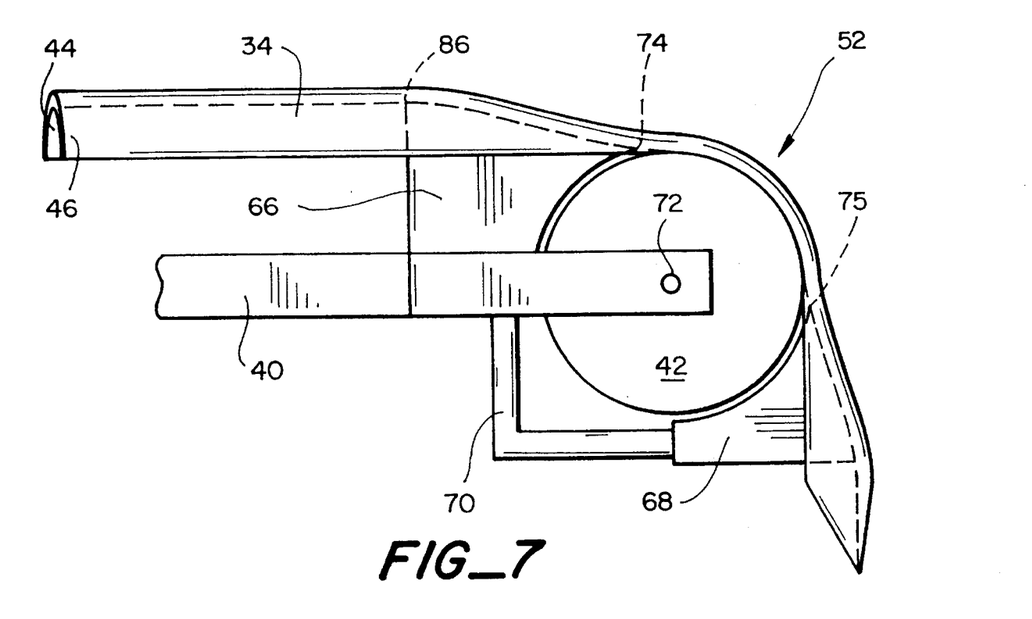
FIG. 7 is an expanded side view of an embodiment of the tape flattening and bending mechanism of FIG. 5.

FIG. 7 shows an expanded view of the preferred embodiment of the deflector for a curved cross section flexible resilient tape stylet. If a flexible resilient tape stylet is used which has a different cross sectional shape, then the deflector 52 may have a different structure, but will perform the same function. The first spreader block 66 contacts the bottom surface of the flexible resilient tape stylet 34 and spreads out the opposed side portions 44, 46 so that the distance between the two opposed side portions 44 and 46 increases and flattens the flexible resilient tape stylet 34 out. Once the flexible resilient tape stylet has reached the end of the first spreader block 66 nearest the roller, the opposed side portions 44 and 46 are flattened out so that they lie in the same plane as the rest of the flexible resilient tape stylet and the flexible resilient tape stylet is temporarily deformed and becomes flexible. The width of the edge 74 of the first spreader block 66, the width of the edge 75 of the second spreader block 68, the flattened width of the flexible resilient tape stylet and the width of the roller 42 are all the same so that the flexible resilient tape stylet is prevented from returning to its rigid configuration until after it has been bent around the roller. After the flattened flexible resilient tape stylet bends itself around the roller 42, the leading edge 75 of the second spreader block contacts the bottom surface of the flexible resilient tape stylet and permits the flexible resilient tape stylet 34 to slowly return to its non-deformed configuration with two opposed side portions. In one embodiment, this non-deformed configuration is with two opposed side portions which are part of a continuous arc as shown in FIG. 3. Thus, when the flexible resilient tape stylet exits the port 60, it is rigid enough to penetrate tissue.

Figure 8:
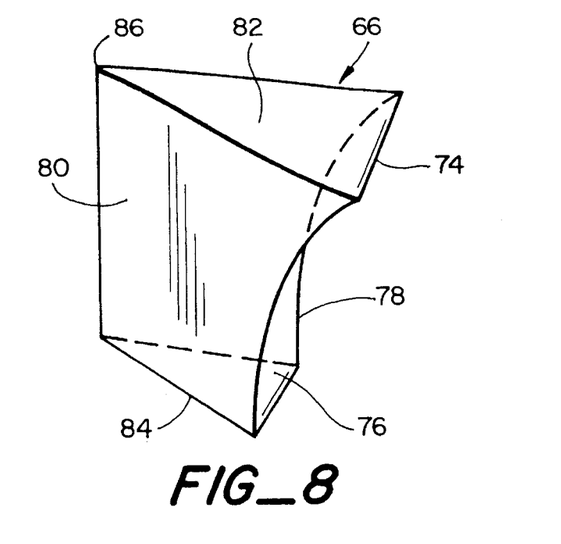
FIG. 8 is an isometric view of the spreader block shown in FIGS. 5 and 7.

FIG. 8 shows an isometric view of the first spreader block for the present invention. The shapes of the spreader blocks 66 and 68 will depend upon the cross sectional shape of the flexible resilient tape stylet. For this embodiment having a curved cross section flexible resilient tape stylet, the first spreader block 66 has a curved front face 76, two slanted side faces 78 and 80 and triangular top and bottom faces 82 and 84. The curved front face 76 allows the first spreader block 66 to be positioned close to the roller 42 without any contact, as shown in FIG. 7 so that the flexible resilient tape stylet can not inadvertently return to its rigid configuration. The first spreader block 66 also has an elevated leading tip 86, which contacts the bottom surface of the flexible resilient tape stylet and spreads the two opposed side portions 44 and 46 outward. The first spreader block 66 also slopes downwards towards the edge 74 which is nearest the roller 42. As described above, the edge 74 of the spreader block nearest the roller is as wide as the roller and as wide as the flattened flexible resilient tape stylet. The second spreader block 68 also would have a similar shape, but would be orientated differently.

Figure 9:
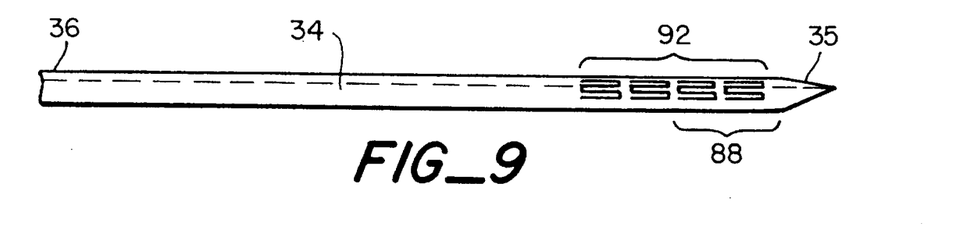
FIG. 9 is a side view of a flexible resilient curved spear tape in accordance with the present invention.

FIG. 9 is a side view of a curved flexible resilient tape stylet of the present invention. The flexible resilient tape stylet 34 has a proximal end 36, a piercing end 88 and two opposed side portions 44 and 46. The proximal end 36 of the flexible resilient tape stylet is connected to said tape stylet connector 32 (shown in FIG. 2). The piercing end 88 of the flexible resilient tape stylet has a sharpened, beveled tip 35 which is used for penetrating tissue in between the catheter location and the target tissue location. The sharpened, beveled tip 35 can be part of the flexible resilient tape stylet or can be attached to the flexible resilient tape stylet after it has been manufactured. A plurality of electrodes 92 are shown near the piercing end 88 of the flexible resilient tape stylet. These electrodes 92 are only located near the piercing end where the flexible resilient tape stylet is within the target tissue. Any healthy tissue, such as the urethra wall, through which the flexible resilient tape stylet must move to get to the target tissue will not be subjected to the microwave or RF treatment. Thus, no sleeve is needed to protect the healthy tissue from the treatment.

The plurality of electrodes 92 are electrically connected to the power supply 31 (shown in FIG. 1). The power supply 31 provides RF or microwave energy to the electrodes 92 which causes heating and eventual death of the target tissue. The method of treating target tissue by RF ablation is described in copending attorney docket no. 5254-003-37 CIP, which is included herein by reference.

The specific details of the power supply for RF ablation systems is further disclosed in copending applications having attorney docket nos. 5254-046-37 CIP and 5254-118-37 CIP which are included herein by reference.

Figure 10:
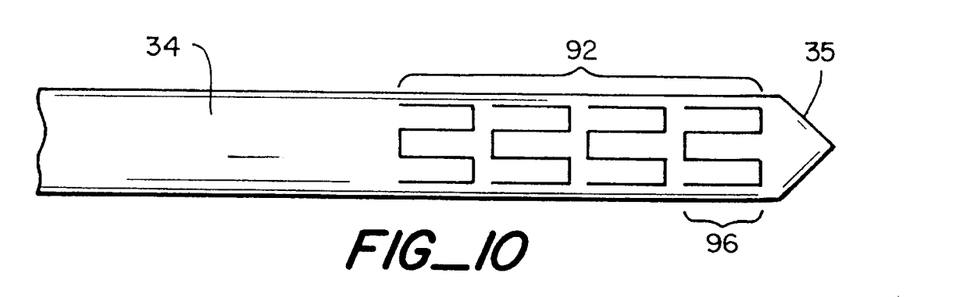
FIG. 10 is a fragmentary top view of an embodiment of the flexible resilient spear tape having multiple electrodes.

FIG. 10 shows a flexible resilient tape stylet having multiple independently energizable electrodes 96. Four electrodes are shown, but the invention is not limited to a particular number of electrodes. These electrodes 96 are connected to separate leads which are all electrically connected to the power supply. Thus, each electrode can be energized independent of any other electrode. These multiple independently energizable electrodes 96 can be energized in a number of ways. For example, a single electrode, like the prior art, can be energized in a monopolar fashion in which the ground electrode (not shown) is located outside the body of the patient. For multiple electrodes, each electrode can be energized independently of each other in a monopolar fashion so that a precise amount of RF or microwave energy can be applied to the target tissue. A problem of prior art systems was that the tissue nearest the RF electrode would receive more RF current and consequently dry out more quickly than the other target tissue which would cause the RF device to shut down. Then the RF electrode would have to be moved and multiple treatments would be required. With the multiple independently energizable electrodes, less energy can be applied to each independent electrode for a longer period of time which will allow more total energy to be applied to the target tissue.

The electrodes can also be energized in a bipolar fashion where the power electrode and the ground electrode are both located within the target tissue. In addition, for four electrodes, two complete bipolar electrode pairs can be used to ablate the target tissue. This configuration would allow for quicker treatment of a large target tissue area. These various electrode energization patterns allow more precise control of the ablative treatment by better controlling the amount of energy applied to the target tissue.

Figure 11:
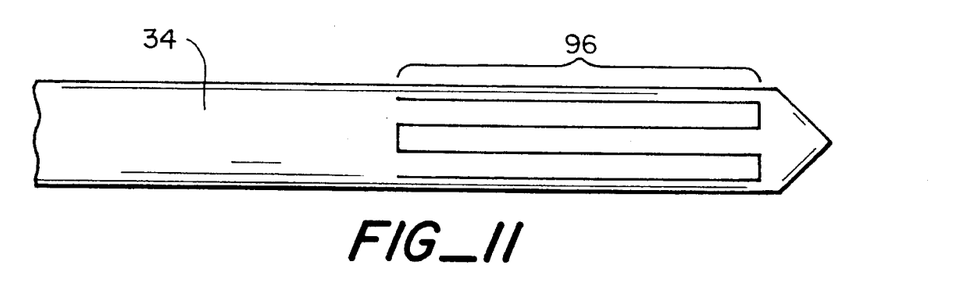
FIG. 11 is a fragmentary top view of an embodiment of the flexible resilient spear tape having a single electrode.
Figure 12:
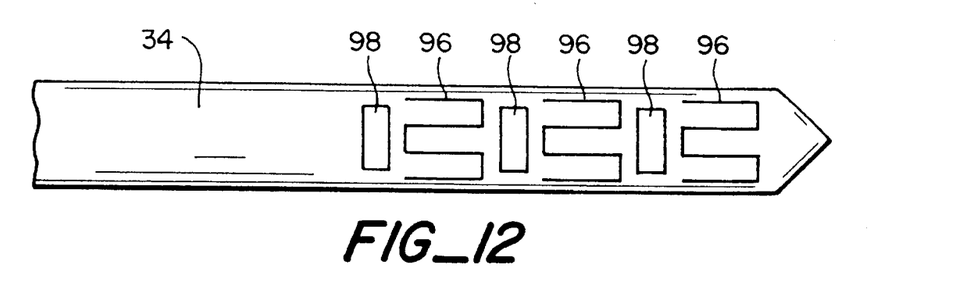
FIG. 12 is a fragmentary top view of an embodiment of the flexible resilient spear tape having multiple electrodes and multiple temperature sensors.

FIG. 11 shows a flexible resilient tape stylet with a single electrode which would operate in a monopolar manner. The single electrode configuration can be utilized for a small amount of target tissue. FIG. 12 shows another embodiment of the flexible resilient tape stylet in which the independently energizable electrodes 96 are combined with a plurality of thermocouples 98. In the configuration shown, a temperature sensor 98 is located near each electrode 96 so that the temperature near every electrode can be accurately measured. The thermocouples 98 are electrically connected to the power supply 31 (shown in FIG. 1). The feedback information from the thermocouples in combination with the various electrode energization patterns permits highly precise amounts of ablative energy to be applied to the target tissue.

Figure 13:
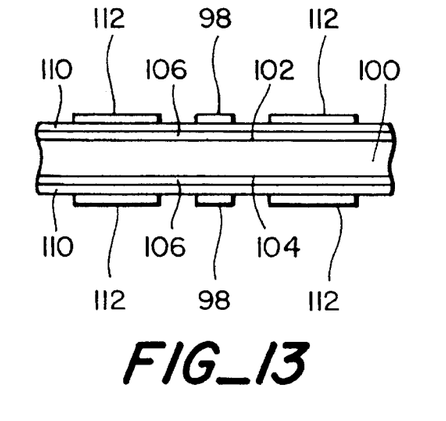
FIG. 13 is a fragmentary side view of an embodiment of flexible resilient spear tape having electrodes bonded to the top and bottom surfaces of the flexible resilient spear tape.
Figure 14:
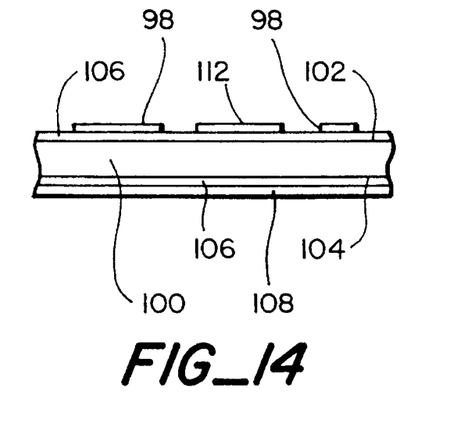
FIG. 14 is a fragmentary side view of an embodiment of flexible resilient spear tape having electrodes bonded to the top surface of the flexible resilient spear tape and a ground electrode bonded to the bottom surface of the flexible resilient spear tape.

FIGS. 13 and 14 show two methods of manufacturing a flexible resilient tape stylet in accordance with the present invention. Initially, for both methods, a flexible resilient substrate 100 is obtained which has the desired non-deformed shape. For these embodiment, a curved cross section flexible resilient substrate will be used. FIG. 13 shows one embodiment of a flexible resilient tape stylet having electrodes on both the top and bottom surfaces of the tape stylet. A first insulating layer 106, having power traces within it, is bonded to the top 102 and bottom 104 surfaces of the substrate 100. The power traces (not shown) carry the power to the separately energizable electrodes and signals from the temperature sensors. A second insulating layer 110 is layered on top of the first insulating layer 106. Then an electrode grid 112 and temperature sensors 98 are deposited on the top 102 and bottom 104 surfaces of the flexible resilient substrate 100 on top of the second insulating layer 110.

FIG. 14 shows another embodiment of a flexible resilient tape stylet in which electrodes are only located on the top surface of the substrate 102. A first insulating layer 106 is bonded to the top 102 and bottom 104 surfaces of the substrate. Next, on the bottom of the substrate 104, a power trace 108 is deposited which carries all of the power to the electrodes and the signals from the sensors. Finally, on the top surface of the substrate 102, an electrode grid 112 and temperature sensors 98 are deposited. Both of the embodiments shown in FIGS. 13 and 14 operate in the same manner.

Figure 15:
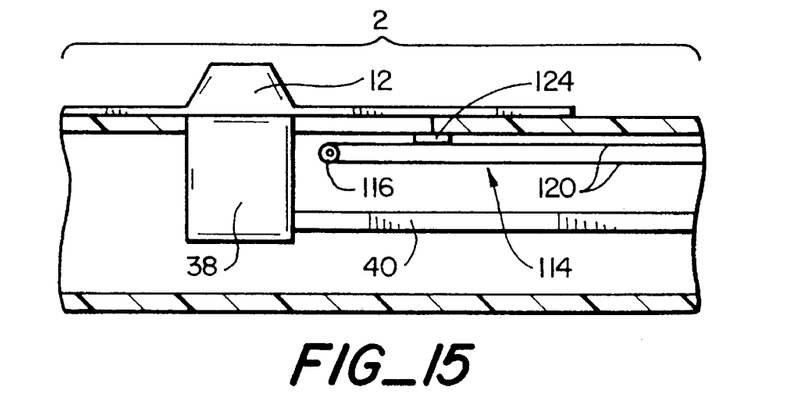
FIG. 15 is a fragmentary cross section of another embodiment of the handle portion having a pulley control mechanism.
Figure 16:
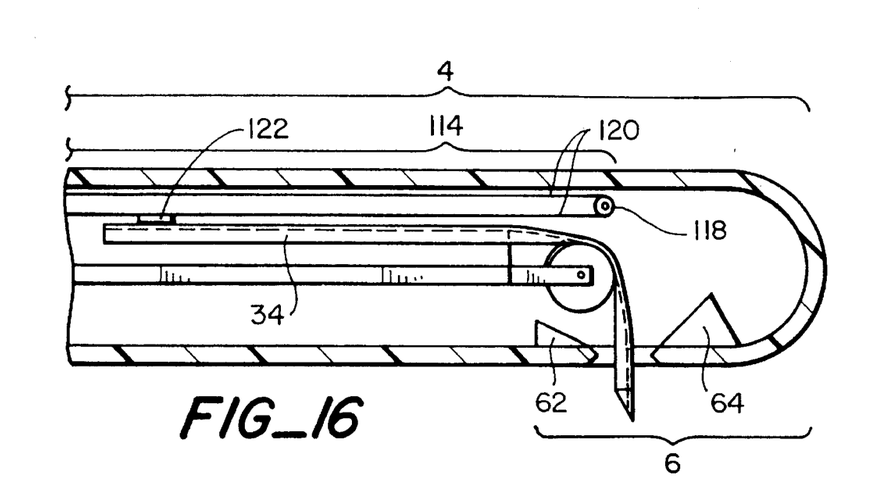
FIG. 16 is an expanded fragmentary cross section of the probe end of an elongated guide which has a pulley control mechanism of FIG. 15.

FIGS. 15 and 16 show another embodiment of the control system housed within the handle 2 and the elongated guide 4 of the present invention. In this embodiment, the roller manual control tab 12 is connected to the roller yoke 40 by the roller connector 38, as before. The tape stylet manual control tab 10, however, is connected to the flexible resilient tape stylet 34 in a different manner. The tab 10 is now connected to a pulley mechanism 114. The pulley mechanism 114 in turn is connected to the flexible resilient tape stylet 34 in any conventional manner, such as welding. The pulley mechanism 114 includes a first pulley 116, a pulley tape 120 and a second pulley 118. As the tape stylet manual control tab 10 is pulled back towards the handle, the pulley tape 120 is pulled back and the flexible resilient tape stylet 34 is extended out of the port 60. Similarly, if the tape stylet manual control tab 10 is pushed forwards towards the elongated guide, the pulley tape 120 is pushed forwards and the flexible resilient tape stylet is retracted back into the elongated guide 4.

Figure 17:
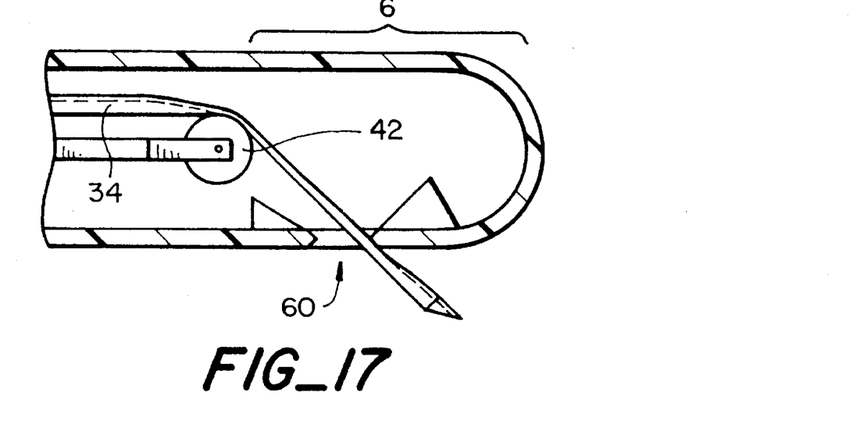
FIG. 17 is a fragmentary cross section of the preferred embodiment of the medical probe when the roller is in a retracted position which causes the flexible resilient spear tape to deflect away from the handle.
Figure 18:
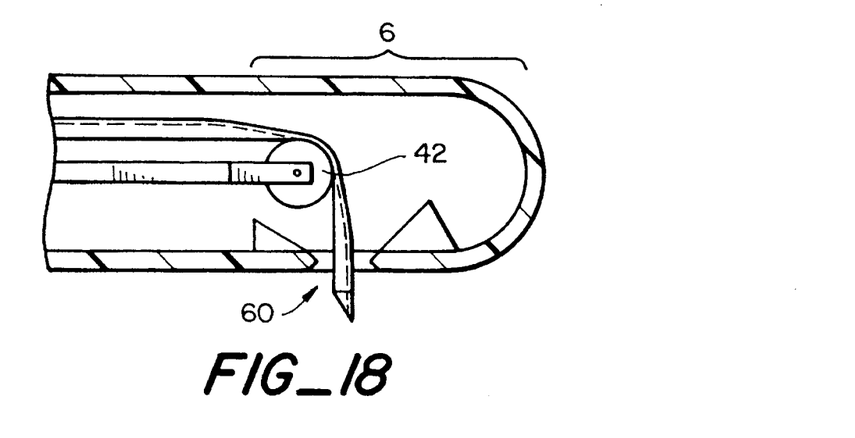
FIG. 18 is a fragmentary cross section of the preferred embodiment of the medical probe when the roller is in a neutral position which causes the flexible resilient spear tape to point straight out from the catheter port.
Figure 19:
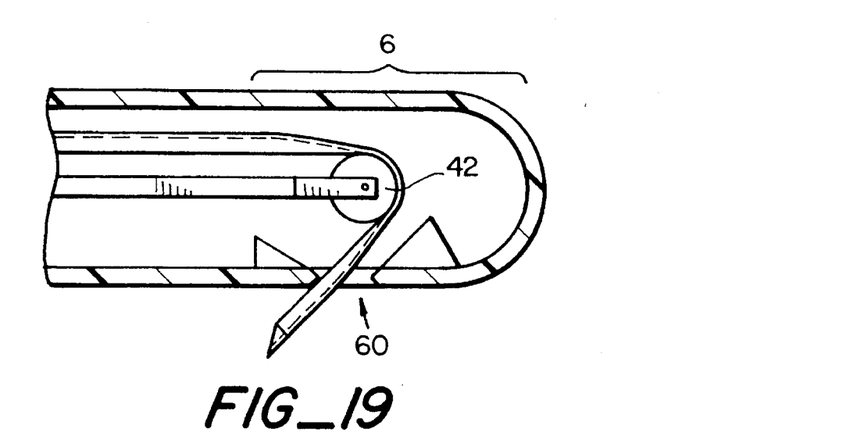
FIG. 19 is a fragmentary cross section of the preferred embodiment of the medical probe when the roller is in an extended position which causes the flexible resilient spear tape to deflect backwards towards the handle.

FIGS. 17, 18, and 19 show the medical probe device of the present invention having the roller 42 in various positions. The roller position depends upon the position of the roller manual control tab 12. FIG. 17 shows the roller 42 in a retracted position. When the roller is in this retracted position, the flexible resilient tape stylet 34 bends around the roller 42 and exits the port 60 in a forward direction as shown. On the other hand, if the roller 42 is in a neutral position, as shown in FIG. 18, then the flexible resilient tape stylet 34 exits the port 60 substantially perpendicular to the probe end 6. Likewise, if the roller 42 is in an extended position, as shown in FIG. 19, then the flexible resilient tape stylet 34 exits the port 60 in a rearward direction as shown. The necessary angle that the flexible resilient tape stylet exits from the port 60 depends on the location of the target tissue relative to the port 60.

To those skilled in the art to which this invention relates, many changes in construction and widely differing embodiments and applications of the invention will make themselves know without departing from the spirit and scope of the invention. The disclosure and the description herein are purely illustrative and are not intended to be in any sense limiting.

We claim:

1. A medical probe device for the treatment by radio frequency ablation of tissue in a prostate of a human male having a urethra with the tissue of the prostate surrounding a portion of the urethra comprising an elongate guide member extending along a longitudinal axis and having proximal and distal extremities, the elongate guide member being sized to be able to enter the urethra and having a length so that when the distal extremity is disposed in the vicinity of the prostate the proximal extremity is outside of the urethra, the elongate guide member having a passageway extending along the longitudinal axis to an opening at the distal extremity, a tape-like stylet disposed in the passageway and having proximal and distal extremities, the stylet having a shape with a transverse cross-section which is generally arcuate for providing column strength to the stylet and being resiliently deformable along its length to an altered shape in which the stylet has a transverse cross-section which is generally planar, at least one electrode mounted on the distal extremity of the stylet, a handle secured to the proximal extremity of the elongate guide member, operative means carried by the handle and connected to the proximal extremity of the stylet for causing longitudinal movement of the stylet in the passageway and means carried by the distal extremity of the elongate guide member for deforming the distal extremity of the stylet to its altered shape for facilitating direction of the distal extremity of the stylet at an angle to the longitudinal axis through the opening and into the tissue of the prostate.

2. A device of claim 1 together with at least one temperature sensing means carried by the distal extremity of the stylet.

3. A device of claim 1 wherein a plurality of electrodes are mounted on the distal extremity of the stylet.

4. A device of claim 3 together with a plurality of temperature sensing means mounted on the distal extremity of the stylet.

5. A device of claim 4 wherein one of the temperature sensing means is mounted on the distal extremity of the stylet in the vicinity of each electrode.

6. A device of claim 1 wherein the means for deforming the distal extremity of the stylet includes a roller having a curved surface in contact with the stylet.

7. A device of claim 6 together with means carried by the handle and connected to the roller for causing movement of the roller longitudinally of the elongate guide member for determining the angle at which the stylet exits the opening.

8. A device of claim 1 wherein the means for deforming the distal extremity of the stylet includes a flat surface disposed at an angle ranging from 90° to less than 180° relative to the longitudinal axis.

9. A device of claim 1 wherein the means for deforming the distal extremity of the stylet includes a flat surface disposed at an angle ranging from 90° to less than 150° relative to the longitudinal axis.

10. A device of claim 1 wherein the means for deforming the distal extremity of the stylet includes a curved surface.

11. A device of claim 1 wherein the means for deforming the distal extremity of the stylet includes two opposed curved surfaces.

12. A device of claim 3 wherein the plurality of electrodes include a pair of bipolar electrodes.

13. A medical probe device comprising an elongate member extending along a longitudinal axis and having a probe end and a handle end, a passageway extending along the longitudinal axis between the handle end and the probe end, a handle connected to the handle end of the elongate member, a flexible resilient tape stylet disposed in the passageway of the elongate member for movement along the longitudinal axis, the tape stylet having two opposed side portions and a piercing extremity, at least one electrode mounted on the piercing extremity of the tape stylet, a lead connected to the at least one electrode, deflector means carried by the probe end of the elongate member and having a deflection surface positioned in the path of longitudinal movement of the tape stylet and at an angle to the longitudinal axis and a roller whereby the tape stylet is deflected sidewise of the longitudinal axis by the deflection surface while moving distally along the longitudinal axis and a controller carried by the handle and having a pair of digit applicators respectively connected to said roller and said tape stylet.

14. A medical probe device for medical treatment of tissue at a treatment site through a natural body opening comprising an elongate guide member extending along a longitudinal axis and having proximal and distal extremities, the elongate guide member having a passageway extending along the longitudinal axis to an opening at the distal extremity, a stylet movably disposed in the passageway and having proximal and distal extremities, the stylet being formed with opposite terminal edges extending longitudinally therealong, the stylet having a transverse cross-section which is arcuate in shape for providing column strength to the stylet and being resiliently deformable so as to have a transverse cross-section which is generally planar in shape for facilitating bending of the stylet, at least one electrode mounted on the distal extremity of the stylet, a handle secured to the proximal extremity of the elongate guide member and means carried by the distal extremity of the elongate guide member for directing the stylet at an angle to the longitudinal axis into the tissue at the treatment site as the stylet is moved longitudinally in the passageway.

15. A device of claim 14 wherein the stylet has opposite first and second surfaces extending between the terminal edges.

16. A device of claim 15 further comprisinq a layer of insulating material disposed on the first surface of the stylet and the at least one electrode mounted on the layer of insulating material.

17. A device of claim 15 wherein at least one electrode is mounted on the first surface at the distal extremity of the stylet and at least one electrode is mounted on the second surface at the distal extremity of the stylet.

18. A device of claim 14 wherein the means for directing the stylet at an angle to the longitudinal axis includes a deflecting surface disposed in the passageway of the elongate guide member at an angle to the longitudinal axis.

19. A device of claim 14 wherein the distal extremity of the stylet is formed with a beveled tip.

20. A method for treating by radio frequency ablation tissue in a prostate of a human male having a urethra extending through the prostate with an elongate guide housing extending along a longitudinal axis and having proximal and distal extremities with a passageway extending from the proximal extremity to an opening in the distal extremity and a longitudinally-extending stylet having proximal and distal extremities and having first and second opposite edges and first and second opposite surfaces extending between the edges, the stylet having a transverse cross-section which is arcuate in shape and being movably disposed in the passageway of the elongate guide member so that the distal extremity of the stylet is in the vicinity of the opening, comprising the steps of introducing the elongate guide member into the urethra so that the distal extremity of the elongate guide member is in the vicinity of the prostate, engaging the distal extremity of the stylet with a deflector surface carried within the passageway of the elongate guide member and disposed at an angle of at least 90° and less than 180° relative to the longitudinal axis so as to direct the distal extremity of the stylet through the opening into the tissue of the prostate and transmitting radio frequency energy into the tissue of the prostate by means of the stylet whereby the arcuate cross-sectional shape of the stylet provides column strength to the stylet for facilitating penetration of the prostate and whereby the stylet is resiliently deformable so as to have a transverse cross-section which is generally planar for facilitating bending of the stylet while being directed into the tissue of the prostate.

21. A method as in claim 20 wherein the deflector surface is disposed at an angle of at least 90° and less than 150° relative to the longitudinal axis.

22. A method as in claim 20 further comprising the step of retracting the distal extremity of the stylet back through the opening into the elongate guide member.

23. A method as in claim 20 wherein the deflector surface is a flat surface.

24. A method as in claim 20 wherein the deflector surface is a curved surface.

25. A method as is claim 20 wherein the deflector surface is a pair of opposed curved surfaces.

* * * * *